US012718360B2

(12) United States Patent
Schwab

(10) Patent No.: US 12,718,360 B2
(45) Date of Patent: Aug. 25, 2026

(54) MECHANISMS FOR BRAIN ANALYSIS

(71) Applicant: KONINKLIJKE PHILIPS N.V., Eindhoven (NL)

(72) Inventor: Evan Schwab, Cambridge, MA (US)

(73) Assignee: Koninklijke Philips N.V., Eindhoven (NL)

( * ) Notice: Subject to any disclaimer, the term of this patent is extended or adjusted under 35 U.S.C. 154(b) by 344 days.

(21) Appl. No.: 18/373,494

(22) Filed: Sep. 27, 2023

(65) Prior Publication Data

US 2024/0119590 A1 Apr. 11, 2024

Related U.S. Application Data

(60) Provisional application No. 63/413,633, filed on Oct. 6, 2022.

(51) Int. Cl.
*G06T 7/00* (2017.01)
*A61B 5/00* (2006.01)
(Continued)

(52) U.S. Cl.
CPC .......... *G06T 7/0012* (2013.01); *A61B 5/0042* (2013.01); *A61B 5/055* (2013.01);
(Continued)

(58) Field of Classification Search
CPC . G06T 7/0012; G06T 7/11; G06T 7/73; G06T 2207/10092; G06T 2207/20021;
(Continued)

(56) References Cited

U.S. PATENT DOCUMENTS 9,404,986 B2 * 8/2016 White .................... G01R 33/48
2010/0309223 A1 * 12/2010 Roth ......................... G06T 5/50
711/E12.001

(Continued)

FOREIGN PATENT DOCUMENTS

CN 111127441 A 5/2020
WO WO-2019126900 A1 * 7/2019 ............... A61B 5/00

(Continued)

OTHER PUBLICATIONS

Xu, C., Neuroth, T., Fujiwara, T., Liang, R., & Ma, K.-L. (2021). A Predictive Visual Analytics System for Studying Neurodegenerative Disease based on DTI Fiber Tracts. ArXiv.org. https://arxiv.org/abs/2010.07047 (Year: 2021).*

(Continued)

*Primary Examiner* — Sumati Lefkowitz
*Assistant Examiner* — Ryan P Potts

(57) ABSTRACT

A method for localizing structural connectivity biomarkers in neurological diseases, includes dividing a diffusion magnetic resonance imaging brain volume into a set of connected brain regions; extracting three-dimensional voxels along fiber connections which structurally connect the connected brain regions, wherein the brain regions comprise bundles of neurons; applying a deep neural network to diffusion magnetic resonance imaging features extracted from the three-dimensional voxels for each set of fiber connections which structurally connect brain regions; outputting a disease classification based on applying the deep neural network; and applying multi-instance learning to predict whether each fiber connection is indicative of a healthy brain or a diseased brain.

17 Claims, 12 Drawing Sheets

(51) Int. Cl.

| | |
|---|---|
| ***A61B 5/055*** | (2006.01) |
| ***G01R 33/56*** | (2006.01) |
| ***G01R 33/563*** | (2006.01) |
| ***G06T 7/11*** | (2017.01) |
| ***G06T 7/73*** | (2017.01) |
| ***G16H 50/20*** | (2018.01) |
| ***G16H 50/30*** | (2018.01) |
| ***G16H 50/50*** | (2018.01) |
| *G16H 50/70* | (2018.01) |

(52) U.S. Cl.

CPC .......... *A61B 5/4088* (2013.01); *A61B 5/7267* (2013.01); *G01R 33/56341* (2013.01); *G06T 7/11* (2017.01); *G06T 7/73* (2017.01); *G16H 50/20* (2018.01); *G16H 50/30* (2018.01); *G16H 50/50* (2018.01); *A61B 2576/026* (2013.01); *G01R 33/5608* (2013.01); *G06T 2207/10092* (2013.01); *G06T 2207/20021* (2013.01); *G06T 2207/20081* (2013.01); *G06T 2207/20084* (2013.01); *G06T 2207/30016* (2013.01); *G06T 2207/30204* (2013.01); *G16H 50/70* (2018.01)

(58) Field of Classification Search

CPC . G06T 2207/20081; G06T 2207/20084; G06T 2207/30016; G06T 2207/30204; A61B 5/0042; A61B 5/055; A61B 5/4088; A61B 5/7267; A61B 2576/026; A61B 5/165; G01R 33/56341; G01R 33/5608; G16H 50/20; G16H 50/30; G16H 50/50; G16H 40/60; G16H 50/70; G16H 30/40

See application file for complete search history.

(56) References Cited

U.S. PATENT DOCUMENTS

| | | | | |
|---|---|---|---|---|
| 2011/0199084 A1* | 8/2011 | Hasan | ................ | G01R 33/5608<br>324/309 |
| 2016/0334489 A1 | 11/2016 | Sperl et al. | | |
| 2022/0011392 A1 | 1/2022 | Schwab et al. | | |

FOREIGN PATENT DOCUMENTS

| | | |
|---|---|---|
| WO | 2019191784 A1 | 10/2019 |
| WO | 2020104457 A1 | 5/2020 |
| WO | 2021156122 A1 | 8/2021 |

OTHER PUBLICATIONS

Zhang, F., et al. J. (2022). TractoFormer: A Novel Fiber-level Whole Brain Tractography Analysis Framework Using Spectral Embedding and Vision Transformers. ArXiv.org. https://arxiv.org/abs/2207.02327 (Year: 2022).*

Scully JL. What is a disease? EMBO Rep. Jul. 2004;5(7):650-3. doi: 10.1038/sj.embor.7400195. PMID: 15229637; PMCID: PMC1299105. (Year: 2004).*

Shao, Junming, et al. "Prediction of Alzheimer's disease using individual structural connectivity networks." Neurobiology of aging 33.12 (2012): 2756-2765. (Year: 2012).*

Graham, Benjamin, Martin Engelcke, and Laurens van der Maaten. "3d semantic segmentation with submanifold sparse convolutional networks." Proceedings of the IEEE Conference on Computer Vision and Pattern Recognition. 2018.

Graham, Benjamin. "Spatially-sparse convolutional neural networks." arXiv preprint arXiv:1409.6070 (2014).

Cohen, Taco S., Mario Geiger, Jonas Koehler, and Max Welling. "Spherical CNNs." arXiv preprint arXiv:1801.10130 (2018).

Kawahara, Jeremy, et al. "BrainNetCNN: convolutional neural networks for brain networks; towards predicting heurodevelopment." NeuroImage 146 (2017): 1038-1049.

McDaniel, Christian and Shannon Quinn. "Developing a Graph Convolution-Based Analysis Pipeline for Multi-Modal Neuroimage Data: An Application to Parkinson's Disease." (2019).

Li et al "A Hybrid Deep Learning Framework for Integrated Segmentation and Registration: Evaluation on Longitudinal White Mattre Tract Changes".

Marzban EN, Eldeib AM, Yassine IA, Kadah YM, for the Alzheimer's Disease Neurodegenerative Initiative (2020) Alzheimer's disease diagnosis from diffusion tensor images using convolutional neural networks. PLoS ONE 15 (3): e0230409. https://doi.org/10.1371/journal.pone.0230409.

Marzullo et al "Classification of Multiple Sclerosis Clinical Profiles via Graph Convolutional Neural Networks" Frontiers in NeuroScience, Jun. 12, 2019.

Cheng et al "Classification of MR Brain Images by Combination of Multi-CNNs for AD Diagnosis" Proc. SPIE 10420, Ninth International Conference on Digital Image Processing (ICDIP2017), 1042042 (Jul. 21, 2017); doi: 10.1117/12.2281808.

Nath et al "Deep Learning Reveals Untapped Information for Local White-Matter Fiber Reconstruction in Diffusion Weighted MRI" Magnetic Resonance Imaging 62 (2019) p. 220-227.

McDaniel et al "Developing a Graph Convolutional Based Analysis Pipeline for Multi-Modal Neuroimage Data: An Application to Parkinson's Disease" Proc. of the 18th Python in Science Conf. (2019).

Sarwar et al "Towards Deep Learning for Connectome Mapping: A Block Decomposition Framework" Neuroimage 212 (2020).

Caiafa "Unified Representation of Tractography and Diffusion-Weighted MRI Data Using Sparse Multidimensional Arrays" 31st Conf. on Neural Information Processing Systems Long Beach CA. 2017.

Zhang et al "Whole Brain White Matter Connectivity Analysis using Machine Learning:an Application to Autism" Neruoimage 2018.

Xi Zhang et al: "Multi-View Graph Convolutional Network and Its Applications on Neuroimage Analysis for Parkinson's Disease", arxiv.org, Cornell University Library, 201 Olin Library Cornell University Ithaca, NY 14853, May 22, 2018 (May 22, 2018), XP081246135.

Song Tzu-An et al: "Graph Convolutional Neural Networks for Alzheimer's Disease Classification", 2019 IEEE 16th International Symposium On Biomedical Imaging (ISBI 2019), IEEE, Apr. 8, 2019 (Apr. 8, 2019), pp. 414-417, XP033576662, DOI: 10.1109/ISBI.2019.8759531.

Liu Mingxia et al: "Landmark-based deep multi-instance learning for brain disease diagnosis", Medical Image Analysis, vol. 43, Jan. 1, 2018 (Jan. 1, 2018), pp. 157-168.

Zhu Wenyong et al: "Dual Attention Multi-Instance Deep Learning for Alzheimer's Disease Diagnosis With Structural MRI", IEEE Transactions on Medical Imaging, IEEE, USA, vol. 40, No. 9, May 3, 2021 (May 3, 2021), pp. 2354-2366.

Zhang F, Daducci A, He Y, Schiavi S, Seguin C, Smith RE, Yeh CH, Zhao T, O'Donnell LJ. Quantitative mapping of the brain's structural connectivity using diffusion MRI tractography: A review. Neuroimage. Apr. 1, 2022;249:118870. doi: 10.1016/j.neuroimage.2021.118870. Epub Jan. 1, 2022. PMID: 34979249; PMCID: PMC9257891.

* cited by examiner

581

681

881

981

MECHANISMS FOR BRAIN ANALYSIS

CROSS REFERENCE TO RELATED APPLICATIONS

This application claims priority to U.S. Provisional Application 63/413,633 filed Oct. 6, 2022, the contents of which are herein incorporated by reference.

BACKGROUND

Diffusion magnetic resonance imaging (dMRI) is a medical imaging modality used to reconstruct and visualize the anatomical network of neuronal fiber tracts in the brain, in vivo. Diffusion magnetic resonance imaging involves using a pattern of magnetic resonance imaging sequences to generate images based on the diffusion of water molecules. Fiber tracts are bundles of nerve fibers connecting brain regions. The brain regions may comprise bundles of neurons. Diffusion magnetic resonance imaging measures directional quantities of water diffusion in the brain by acquiring a set of diffusion weighted images to estimate the orientation of bundles of neurons at each voxel of a brain volume. These orientation estimations are modelled by spherical probability distribution functions (PDFs) such as a three-dimensional Gaussian distribution known as a diffusion tensor in diffusion tensor imaging (DTI) or a non-parametric orientation distribution function in high angular resolution diffusion imaging. Fiber tracts are then reconstructed by following the peaks of these spherical probability distribution functions in each voxel.

SUMMARY

According to an aspect of the present disclosure, a method for localizing structural connectivity biomarkers in neurological diseases includes dividing a diffusion magnetic resonance imaging brain volume into a set of connected brain regions; extracting three-dimensional voxels along fiber connections which structurally connect the connected brain regions, wherein the brain regions comprise bundles of neurons; applying a deep neural network to diffusion magnetic resonance imaging features extracted from the three-dimensional voxels for each set of fiber connections which structurally connect brain regions; outputting a disease classification based on applying the deep neural network; and applying multi-instance learning to predict whether each fiber connection is indicative of a healthy brain or a diseased brain.

According to another aspect of the present disclosure, a system for localizing structural connectivity biomarkers in neurological diseases includes a memory that stores instruction; a display; and a processor that executes the instructions. Based on the processor executing the instructions, the system is caused to: divide a diffusion magnetic resonance imaging brain volume into a set of connected brain regions; extract three-dimensional voxels along fiber connections which structurally connect the connected brain regions, wherein the brain regions comprise bundles of neurons; apply a deep neural network to diffusion magnetic resonance imaging features extracted from the three-dimensional voxels for each set of fiber connections which structurally connect brain regions; output a disease classification based on applying the deep neural network; and apply multi-instance learning to predict whether each fiber connection is indicative of a healthy brain or a diseased brain.

According to another aspect of the present disclosure, a controller for localizing structural connectivity biomarkers in neurological diseases includes a memory that stores instruction, and a processor that executes the instructions. Based on the processor executing the instructions, the controller is caused to: divide a diffusion magnetic resonance imaging brain volume into a set of connected brain regions; extract three-dimensional voxels along fiber connections which structurally connect the connected brain regions, wherein the brain regions comprise bundles of neurons; apply a deep neural network to diffusion magnetic resonance imaging features extracted from the three-dimensional voxels for each set of fiber connections which structurally connect brain regions; output a disease classification based on applying the deep neural network; and apply multi-instance learning to predict whether each fiber connection is indicative of a healthy brain or a diseased brain.

According to yet another aspect of the present disclosure, a method for classifying brain diseases includes generating a spherical diffusivity profile for each of a plurality of voxel locations in a three-dimensional model of a brain, wherein the three-dimensional model of the brain comprises segmented brain regions and each segmented brain region comprises bundles of neurons connected by fiber tracts; applying a spherical convolutional neural network to each spherical diffusivity profile to output a feature vector; for each voxel location for fiber tracts connecting a pair of brain regions in the three-dimensional model of the brain, inputting the voxel and the feature vector from the spherical convolutional neural network to a sparse three-dimensional convolutional neural network; for each voxel location for fiber tracts connecting the pair of brain regions in the three-dimensional model of the brain, outputting from the sparse three-dimensional convolutional neural network a feature vector of reduced input size; for a plurality of voxel locations for fiber tracts that connect N region pairs, concatenating feature vectors from the sparse three-dimensional convolutional neural network to form a single feature vector; feeding the single feature vector into a set of fully connected layers; and outputting, from the set of fully connected layers, a class prediction. The method may be implemented by a system, a controller and/or a computer-readable medium.

According to still another aspect of the present disclosure, a method for classifying diffusion magnetic resonance imaging using sparse three-dimensional convolutional neural networks includes segmenting brain regions of interest from a digital model of a brain; reconstructing fiber tracts between the brain regions of interest from structural diffusion magnetic resonance imaging data by following peaks of spherical probability distribution functions in each of a plurality of voxels in the digital model of the brain; compute an orientation distribution function in each voxel in the digital model of the brain; applying a plurality of sparse three-dimensional convolutional neural networks to the segmented brain regions of interest, to the reconstructed fiber tracts, and to features from the orientation distribution function of the brain; outputting, from each of the sparse three-dimensional convolutional neural networks, a feature vector; inputting the feature vector from each of the sparse three-dimensional convolutional neural networks to a graphical convolutional neural network; and classifying disease for the brain based on applying the graphical convolutional neural network to the feature vector from each of the sparse three-dimensional convolutional neural network.

BRIEF DESCRIPTION OF THE DRAWINGS

The example embodiments are best understood from the following detailed description when read with the accompanying drawing figures. It is emphasized that the various features are not necessarily drawn to scale. In fact, the dimensions may be arbitrarily increased or decreased for clarity of discussion. Wherever applicable and practical, like reference numerals refer to like elements.

DETAILED DESCRIPTION

Figure 1:
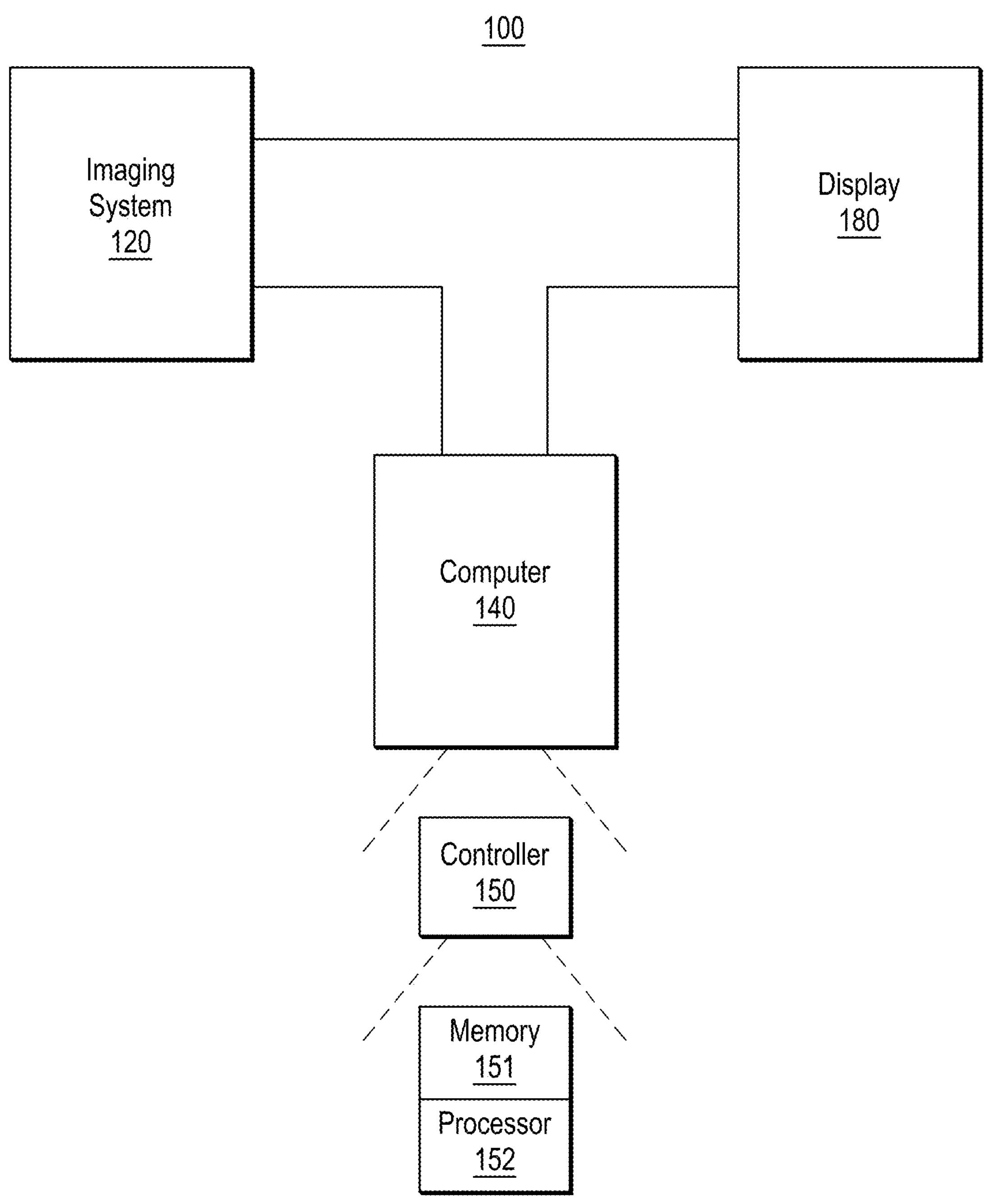
FIG. 1 illustrates a system for mechanisms for brain analysis, in accordance with a representative embedment.

In the following detailed description, for the purposes of explanation and not limitation, representative embodiments disclosing specific details are set forth in order to provide a thorough understanding of embodiments according to the present teachings. However, other embodiments consistent with the present disclosure that depart from specific details disclosed herein remain within the scope of the appended claims. Descriptions of known systems, devices, materials, methods of operation and methods of manufacture may be omitted so as to avoid obscuring the description of the representative embodiments. Nonetheless, systems, devices, materials and methods that are within the purview of one of ordinary skill in the art are within the scope of the present teachings and may be used in accordance with the representative embodiments. It is to be understood that the terminology used herein is for purposes of describing particular embodiments only and is not intended to be limiting. Definitions and explanations for terms herein are in addition to the technical and scientific meanings of the terms as commonly understood and accepted in the technical field of the present teachings.

It will be understood that, although the terms first, second, third etc. may be used herein to describe various elements or components, these elements or components should not be limited by these terms. These terms are only used to distinguish one element or component from another element or component. Thus, a first element or component discussed below could be termed a second element or component without departing from the teachings of the inventive concept.

As used in the specification and appended claims, the singular forms of terms 'a,' 'an' and 'the' are intended to include both singular and plural forms, unless the context clearly dictates otherwise. Additionally, the terms "comprises", and/or "comprising," and/or similar terms when used in this specification, specify the presence of stated features, elements, and/or components, but do not preclude the presence or addition of one or more other features, elements, components, and/or groups thereof. As used herein, the term "and/or" includes any and all combinations of one or more of the associated listed items.

Unless otherwise noted, when an element or component is said to be "connected to," "coupled to," or "adjacent to" another element or component, it will be understood that the element or component can be directly connected or coupled to the other element or component, or intervening elements or components may be present. That is, these and similar terms encompass cases where one or more intermediate elements or components may be employed to connect two elements or components. However, when an element or component is said to be "directly connected" to another element or component, this encompasses only cases where the two elements or components are connected to each other without any intermediate or intervening elements or components.

The present disclosure, through one or more of its various aspects, embodiments and/or specific features or sub-components, is thus intended to bring out one or more of the advantages as specifically noted below.

As described herein, end-to-end deep neural networks may be applied for analyzing brain imagery. For example, end-to-end deep neural networks may be applied to brain images to predict whether individual fiber connections which connect connected brain regions are indicative of a healthy brain or a diseased brain. As another example, end-to-end deep neural networks may be applied to brain images to output a class prediction for the brain as a whole. As yet another example, end-to-end deep neural networks may be applied to brain images to classify a disease for the brain. The end-to-end deep neural networks may include different types of neural networks including a spherical convolutional neural network, a sparse three-dimensional convolutional neural network, and/or a graphical convolutional neural network.

FIG. 1 illustrates a system 100 for mechanisms for brain analysis, in accordance with a representative embodiment.

The system 100 in FIG. 1 is a system for mechanisms for brain analysis and includes components that may be provided together or that may be distributed. The system 100 includes an imaging system 120, a computer 140, and a display 180. The computer 140 includes at least a controller 150, and the controller 150 includes at least a memory 151 and a processor 152.

The imaging system 120 is a medical imaging system and may be used to capture images of a brain. As an example, the imaging system 120 may be a magnetic resonance imaging system. Magnetic resonance imaging is used to form images of the brain using strong magnetic fields, magnetic field gradients, and radio waves. The imaging system 120 may be provided separate from the computer 140. For example, the imaging system 120 may comprise a diffusion magnetic resonance imaging system at a facility dedicated to medical imaging, and may provide diffusion magnetic resonance imaging images to the computer 140 over a network, either automatically or selectively on-demand when the end-to-end deep neural networks described herein are to be applied by the computer 140 to the diffusion magnetic resonance imaging images generated by the imaging system 120.

The computer 140 receives images of the brain from the imaging system 120, and performs processes that result in supplemented imagery of the brain being displayed on the display 180. A computer that can be used to implement the computer 140 is depicted in FIG. 11, though a computer 140 may include more elements than depicted in FIG. 1 and more or fewer elements than depicted in FIG. 11. The computer 140 may be implemented as a stand-alone computer for a single user or office, a centralized computer such as a server for a facility that includes multiple users or offices, or even a centralized computer in a cloud configuration where the computer 140 provides on-demand processing services of the types described herein for multiple facilities. In some examples, the computer 140 is representative of multiple, distributed, computers, that individually or cooperatively implement processing services of the types described herein, such as in a cloud configuration. The computer 140 may be used to implement the end-to-end deep neural network shown in FIG. 4, the end-to-end deep neural network shown in FIG. 7, and/or the end-to-end deep neural network shown in FIG. 10A. The computer 140 may also perform or control performance of methods shown herein and described with respect to FIG. 3B, FIG. 5B, and FIG. 10B.

The memory 151 stores instructions and the processor 152 executes the instructions. The instructions executed by the processor 152 may include instructions to implement trained artificial intelligence models including the variety of neural networks described herein. In some embodiments, the memory 151 and the processor 152 may be representative of multiple memory/processor combinations. In some embodiments, one or more artificial intelligence models may be executed on a chip by a processor dedicated to implementing artificial intelligence.

The controller 150 may also include interfaces, such as a first interface, a second interface, a third interface, and a fourth interface. One or more of the interfaces may include ports, disk drives, wireless antennas, or other types of receiver circuitry that connect the controller 150 to other electronic elements. One or more of the interfaces may also include user interfaces such as buttons, keys, a mouse, a microphone, a speaker, a display separate from the display 180, or other elements that users can use to interact with the controller 150 such as to enter instructions and receive output. The controller 150 may perform some of the operations described herein directly and may implement other operations described herein indirectly. For example, the controller 150 may indirectly control some operations such as by generating and transmitting content to be displayed on the display 180. The controller 150 may directly control other operations such as logical operations performed by the processor 152 executing instructions from the memory 151 based on input received from electronic elements and/or users via the interfaces. Accordingly, the processes implemented by the controller 150 when the processor 152 executes instructions from the memory 151 may include steps not directly performed by the controller 150.

The display 180 may be local to the computer 140 or may be remotely connected to the computer 140. The display 180 may be connected to the computer 140 via a local wired interface such as an Ethernet cable or via a local wireless interface such as a Wi-Fi connection. The display 180 may be interfaced with other user input devices by which users can input instructions, including mouses, keyboards, thumbwheels and so on. The display 180 may be a monitor such as a computer monitor, a display on a mobile device, an augmented reality display, a television, an electronic whiteboard, or another screen configured to display electronic imagery. The display 180 may also include one or more input interface(s) such as those noted above that may connect to other elements or components, as well as an interactive touch screen configured to display prompts to users and collect touch input from users. The display 180 may be configured to display any of the types of images and imagery described herein, such as images of brain volumes including brain regions and fiber connections which structurally connect the brain regions.

Figure 2:
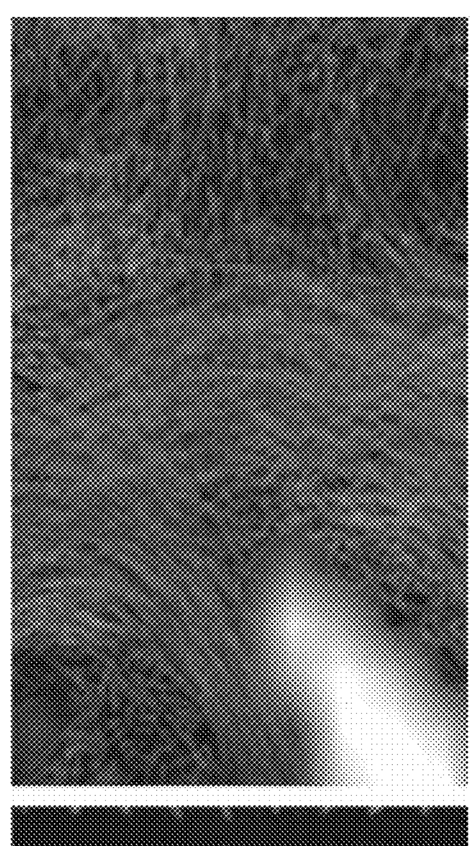
FIG. 2 illustrates orientation distribution functions and fiber tracts reconstructed from tracking peak directions of orientation distribution functions in mechanisms for brain analysis, in accordance with a representative embodiment.
Figure 2:
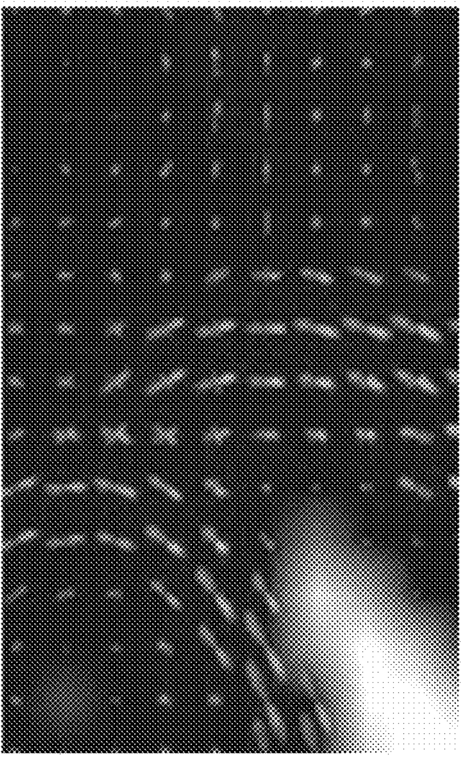

FIG. 2 illustrates orientation distribution functions and fiber tracts reconstructed from tracking peak directions of orientation distribution functions in mechanisms for brain analysis, in accordance with a representative embodiment.

FIG. 2 illustrates an example of orientation distribution functions and the resulting fiber tracts in the human brain. The orientation distribution functions are shown in the left in FIG. 2. The fiber tracts reconstructed from tracing the peak directions of orientation distribution functions are shown on the right in FIG. 2.

The orientation distribution functions and resulting fiber tracts in FIG. 2 are shown on a user interface 281, such as on a display 180 in FIG. 1. Technology for orientation distribution functions is used for analyzing anatomical brain connections, studying neurological and psychological disorders and discovering biomarkers for early detection of diseases such as Alzheimer's disease. Diffusion magnetic resonance imaging analysis may involve extracting hand-crafted features that are analytically computed from a pre-defined diffusion model. Examples of the pre-defined diffusion model include fractional anisotropy and mean diffusivity calculated from the eigenvalues of a diffusion tensor. Fractional anisotropy is an example of diffusion magnetic resonance imaging diffusivity features, and provides a scalar value for each voxel between zero and one. The scalar value indicates degree of anisotropy of a diffusion process. The hand-crafted features give an indication of the amount of diffusivity or integrity of a fiber in each voxel. In terms of connectivity analysis, features may include hand-crafted connectivity metrics from fiber tractography, such as the number, length, or density of fibers that connect different regions of interest. Additional features may include averaging fractional anisotropy along the voxels occupied by the fiber tracts.

In a first set of embodiments, described below, structural connectivity biomarkers of a neurological disease may be localized using multi-instance learning of fiber tract connections that connect brain regions in a brain. Fiber tracts within structural connectivity maps between brain regions may be identified in a brain atlas. Important fiber tracts may be identified within the multi-instance learning framework for the joint localization and classification of neurological disease.

Multi-instance learning (MM) is a variation of supervised learning and is used to address problems in the absence of complete knowledge of labels of individual training instances. In supervised learning, every training instance is assigned a discrete or real-valued label. In multi-instance learning, the discrete or real-valued labels are assigned to bags of multiple instances. In an application of multi-instance learning using binary labelling, a bag is labeled positive if at least one instance in that bag is positive, and the bag is labeled negative if all the instances in that bag are negative. The labeled bags are the training data, and multi-instance learning is used to classify unseen instances in the bags based on the labeled bags as the training data.

A deep neural network is an artificial neural network with multiple hidden layers between the input layer and the output layer. Similar to shallow artificial neural networks, deep neural networks can model complex non-linear relationships. A deep neural network may be applied to diffusion magnetic resonance imaging features extracted from three-dimensional voxels along fiber tracts which structurally connect brain regions of interest. In this way, an end-to-end deep learning pipeline takes diffusion magnetic resonance imaging diffusivity features as input for each set of fiber connections and outputs a disease classification. One aspect for this first set of embodiments is the incorporation of multi-instance learning to localize which fiber tract connections were influential in determining the disease classification. The weightings of each fiber tract connection may be used to provide a heat map visualization along each connection either in the native brain space or within a graphical connectome visualization.

Figure 3A:
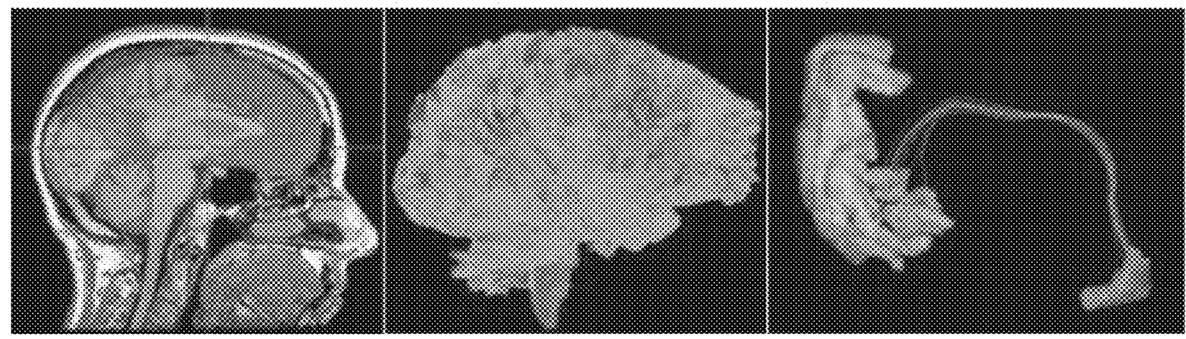
FIG. 3A illustrates brain segmentation of gray matter regions of interest, a structural connectivity tractogram of white matter fiber tracts, and a sample fiber tract connection between two region of interest volumes in mechanisms for brain analysis, in accordance with a representative embodiment.

FIG. 3A illustrates brain segmentation of gray matter regions of interest, a structural connectivity tractogram of white matter fiber tracts, and a sample fiber tract connection between two region of interest volumes in mechanisms for brain analysis, in accordance with a representative embodiment.

In FIG. 3A, brain segmentation of gray matter regions of interest is shown on the left. A structural connectivity tractogram of white matter fiber tracts is shown in the middle. One sample fiber tract connection between two region of interest volumes is shown on the right. A tractogram is a two-dimensional or three-dimensional image visually representing nerve tracts and resulting from modeling using data from diffusion magnetic resonance imaging. The brain segmentation, structural connectivity tractogram, and sample fiber tract in FIG. 3A are shown on a user interface 381, such as on a display 180 in FIG. 1.

Figure 3B:
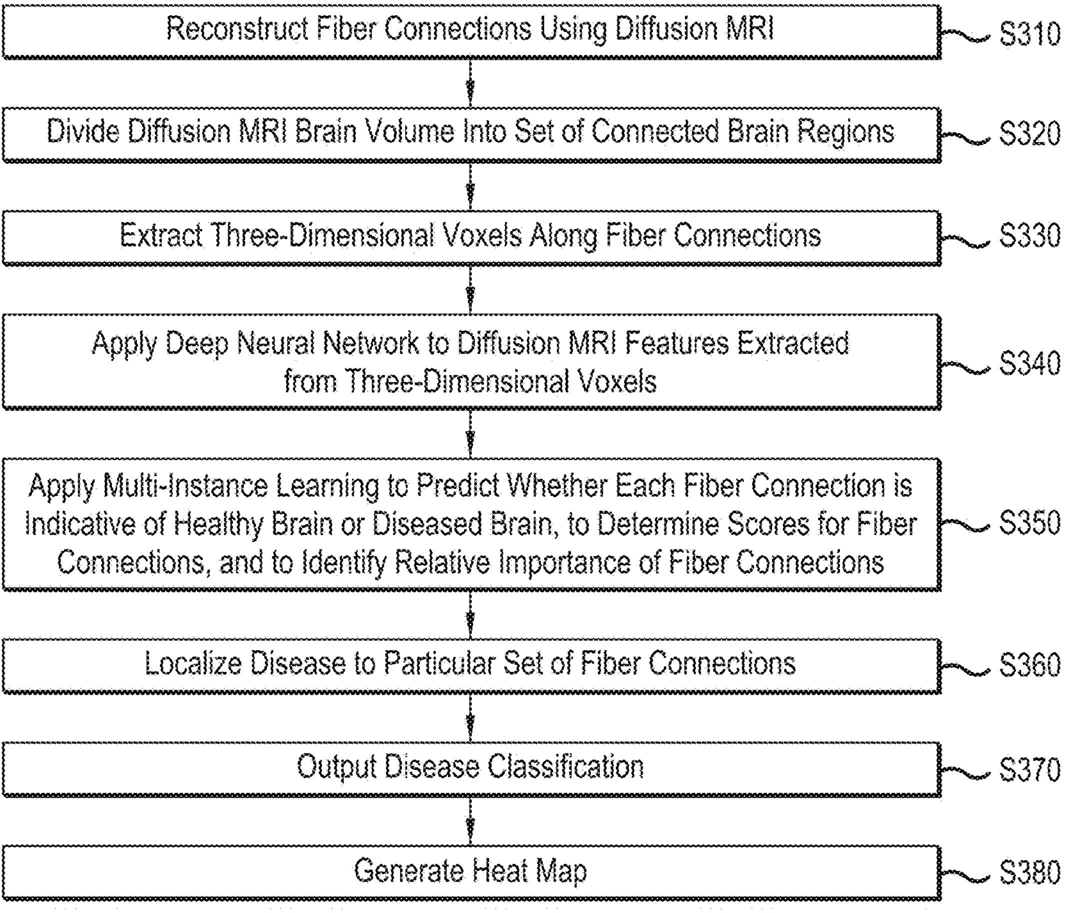
FIG. 3B illustrates a method for mechanisms for brain analysis, in accordance with a representative embodiment.

FIG. 3B illustrates a method for mechanisms for brain analysis, in accordance with a representative embedment.

At S310, fiber connections are reconstructed using diffusion magnetic resonance imaging. The fiber connections may be reconstructed by the computer 140 using diffusion magnetic resonance imaging images from the imaging system 120.

At S320, a diffusion magnetic resonance imaging brain volume is divided into a set of connected brain regions. For example, the computer 140 may apply an image analysis program to the diffusion magnetic resonance imaging images to divide the diffusion magnetic resonance imaging brain volume. The image analysis program may identify the brain regions according to one or more characteristics of brain regions that appear in the diffusion magnetic resonance imaging images. The image analysis program may identify connections according to one or more characteristics of connections that appear in the diffusion magnetic resonance imaging images. Any individual brain region may appear in a single section resulting from the dividing, or may appear in multiple sections resulting from the dividing.

At S330, three-dimensional voxels along fiber connections are extracted. The three-dimensional voxels may correspond to data for features such as a voxel value, a set of coordinates of the voxel, a label automatically assigned to the fiber connection along which the voxel is included, and any other relevant information.

At S340, a deep neural network is applied to diffusion magnetic resonance imaging features extracted from the three-dimensional voxels. The deep neural network may be applied by the computer 140. The deep neural network is a trained deep neural network The features may be diffusion magnetic resonance imaging diffusivity features. For example, diffusivity features may include fractional anisotropy (FA).

At S350, multi-instance learning is applied to predict whether each fiber connection is indicative of a healthy brain or a diseased brain, to determine scores for fiber connections, and to identify relative importance of fiber connections. The multi-instance learning may be applied by the computer 140. In multi-instance learning described herein, data is broken into a set of smaller parts or instances which are collectively used to understand the local aspects that give the data its class label. In the first set of embodiments, the data may be from a diffusion magnetic resonance imaging brain volume with fiber tractography which is divided into the set of structural connections between each region of interest in the brain atlas. For the task of binary image classification (e.g., neurological disease vs normal), a brain volume may be classified as positive if the brain volume has the disease and negative if the brain volume does not. The goal of multi-instance learning in the first set of embodiments is to predict the label of each fiber connection as being normal or indicative of the disease, thereby localizing the disease to a particular set of fiber connections, and relate these connection predictions back to the full tractogram using the global volume labels from training.

As an example, for a brain volume with no disease, all of the connections will be healthy, and so must all have negative labels. Alternatively, for a brain volume with a disease, at least one of the fiber connections is assumed to be abnormal and so will have a positive label while the rest will again have negative labels. In this way, which fiber tracts are normal and which are indicative of the disease can be learned. The application of multi-instance learning at S350 may be considered a weakly supervised problem because the images have training labels, but the instances, i.e., fiber connections, do not.

As an example, applying multi-instance learning at S350 may include processing a diffusion magnetic resonance imaging volume using fiber tractography into a set of fiber connections that connect a set of brain regions delineated by a brain atlas. The multi-instance learning may be applied by a deep neural network, a Sigmoid layer which produces a probabilistic class score for each fiber connection, and a final multi-instance learning layer which relates fiber connection scores to an image of the brain. In some embodiments, a maximum score over all fiber connections may be determined.

In some embodiments, the computer 140 in the system of FIG. 1 may output a brain class prediction at S350 based on the maximum score. Furthermore, in some embodiments, applying the multi-instance learning at S350 may include outputting a set of fiber connection locations and scores providing a connection-wise probabilistic location of the disease biomarker. The connection-wise probabilistic location of the disease biomarker may include a probability of a fiber connection location indicating a biomarker of disease. The connection-wise probabilistic location may be output by a Sigmoid layer of the multi-instance learning algorithm.

At S360, disease is localized to a particular set of fiber connections. The localizing at S360 may be performed by the computer 140, and may include comparing the probabilities for fiber connection locations to a threshold. The localizing may also involve pattern matching, such as checking whether any fiber connection location with a probability above a threshold is adjacent to at least one more fiber connection location with a probability above the threshold, so that outliers may be highlighted or subject to additional analysis.

At S370, a disease classification is output. The disease classification may be binary, such as diseased or not diseased. Alternatively, the disease classification may be scaled, such as on a scale of 1 to 5 or 1 to 10.

At S380, a heat map is generated. As an example, weightings of fiber connections may be determined to identify the relative importance of fiber connections in contributing to the disease. The heat map may be generated to visualize the relative importance of fiber connections based on the weightings. The weightings may be probability scores from 0 to 1 for each fiber connection, which is a result of using the maximum score, i.e., max pooling, as the MTh aggregation function. In some other embodiments, the weightings may all add up to 1, which is a result of using an attention layer as the MIL aggregation function.

Although S340 and S350 are shown as separate features in FIG. 3, the deep neural network applied at S340 may also be applied as part of the multi-instance learning at S350 in some embodiments.

Figure 4:
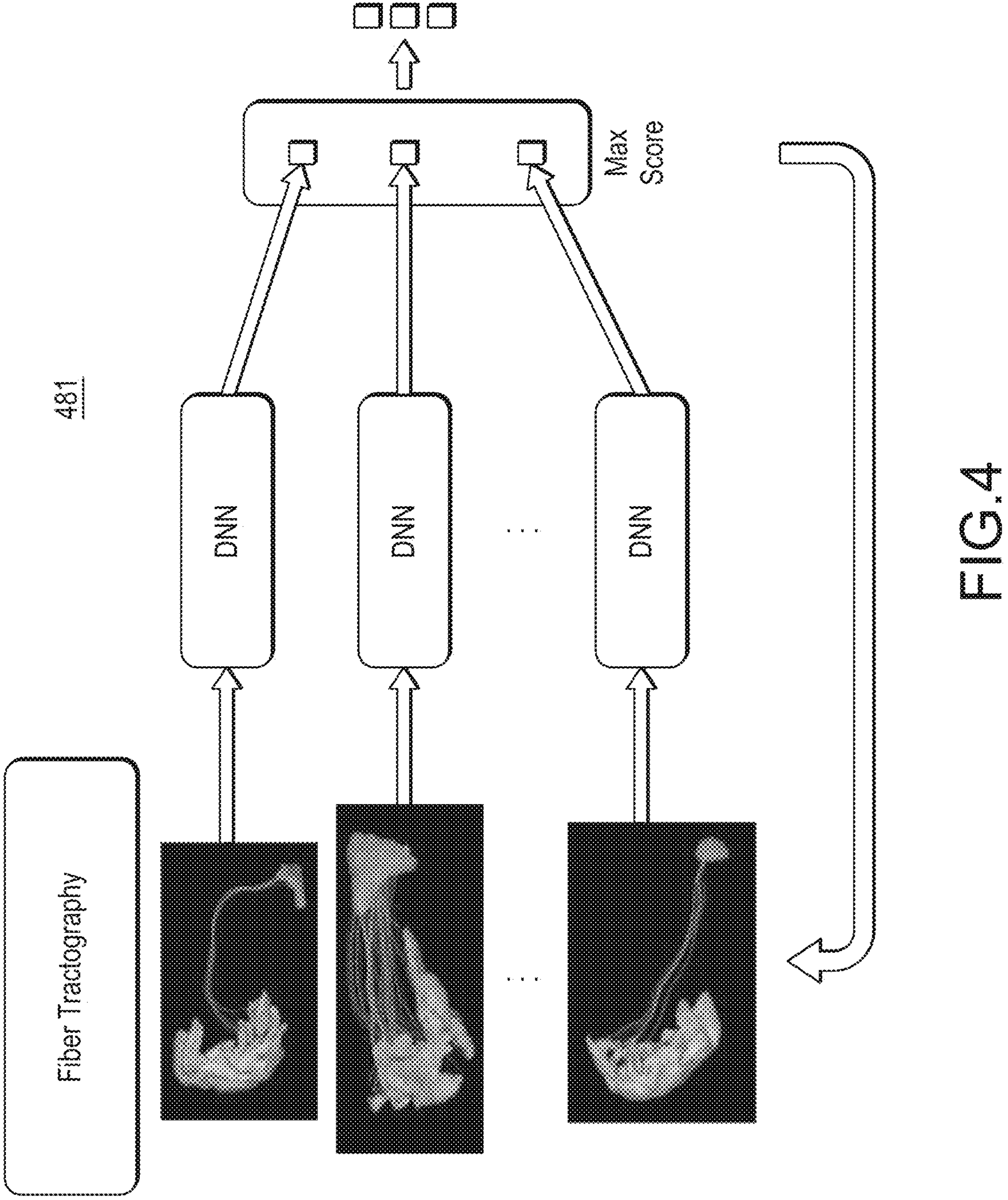
FIG. 4 illustrates a multi-instance learning end-to-end deep neural network for mechanisms for brain analysis, in accordance with a representative embodiment.

FIG. 4 illustrates a multi-instance learning end-to-end deep neural network for mechanisms for brain analysis, in accordance with a representative embodiment.

The end-to-end deep neural network shown in FIG. 4 may be implemented as a deep multi-instance learning algorithm executed on the computer 140 in FIG. 1. The end-to-end deep neural network in FIG. 4 is shown as on a user interface 481, such as on a display 180 in FIG. 1. The multi-instance learning end-to-end deep neural network in FIG. 4 is for neurological diseases classification and fiber tract localization.

Starting on the left in FIG. 4, a diffusion magnetic resonance imaging volume is processed using fiber tractography into a set of fiber tracts that connect a set of regions of interest delineated by a brain atlas. The deep multi-instance learning network may consist of three main components: 1) a deep neural network, 2) a Sigmoid layer which produces a probabilistic class score for each fiber tract, and 3) a final multi-instance learning layer which relates the tract scores to the image. The fiber tract connections with the overall maximum scores may be chosen. For negative volumes, the max layer drives the max fiber tract score, and therefore all fiber tract scores, towards 0. Thus, similar looking normal fiber tracts in diseased brain volumes are also driven towards 0 and positive fiber tracts are driven towards 1. In some other embodiments, an attention layer is used instead of max pooling to produce a weighted sum of each of the fiber connection scores, whereby the weights are learned as parameters within the deep neural network.

The inputs of the multi-instance learning algorithm in FIG. 4 are entirely data for fiber tract connections of a brain volume. The outputs of the multi-instance learning algorithm in FIG. 4 are: 1) a brain class prediction equal to the maximum fiber tract score prediction, and 2) a set of fiber tract locations and scores providing a connection-wise probabilistic localization of the disease biomarker. The outputs are particularly amenable to generating a heat map to visualize the relative importance of fiber connections based on the weightings.

In a second set of embodiments, structural connectivity maps between brain regions identified in a brain atlas may be processed within a deep learning framework for the classification of neurological disease. In deep learning, a convolutional neural network a class of artificial neural network (ANN) and is most commonly applied to analyze visual imagery. Convolutional neural networks assemble patterns of increasing complexity using smaller and simpler patterns embossed in the filters. Convolutional neural networks learn to optimize the filters through automated learning. Spherical convolutional neural networks are applied to spherical signals instead of grid signals. In the second set of embodiments, spherical convolutional neural networks are applied to diffusivity profiles such as fiber orientation distributions estimated at every voxel and combined with sparse three-dimensional convolutional neural networks applied to voxels along fiber tracts which structurally connect brain regions of interest. In this way, an end-to-end deep learning pipeline takes diffusion magnetic resonance imaging spherical diffusivity profiles, such as fiber orientation distribution functions, as input for each set of fiber connections and outputs a disease classification. In addition, because each fiber connection is taken as multiple inputs to the network, using a gradient based saliency mapping, the contribution of each fiber connection and each fiber orientation distribution function to the end classification may be visualized.

As noted above, in terms of connectivity analysis, features may include hand-crafted connectivity metrics from fiber tractography, such as the number, length, or density of fibers that connect different regions of interest. Additional features may include averaging fractional anisotropy along the voxels occupied by the fiber tracts. However, these features do not incorporate small spatial variations along long fiber tracts over the brain.

Figure 5A:
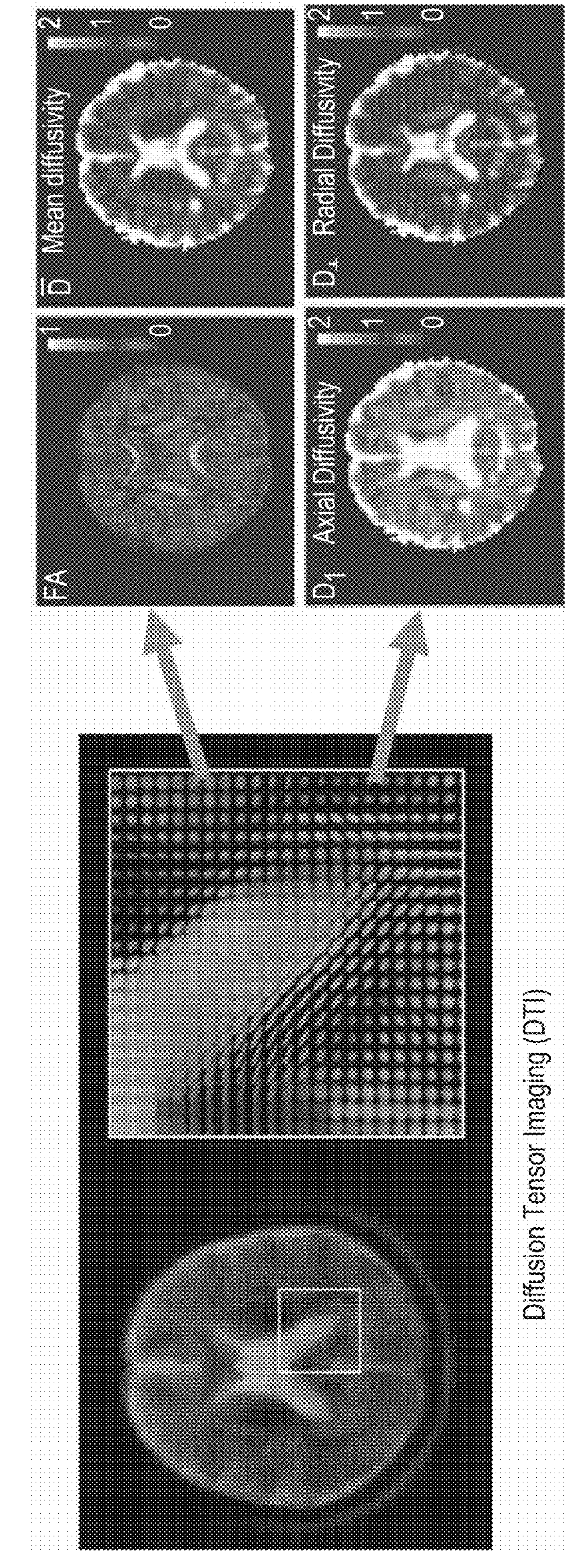
FIG. 5A illustrates hand-crafted diffusion tensor imaging feature maps extracted from eigenvalues of diffusion tensors for mechanisms for brain analysis, in accordance with a representative embodiment.

FIG. 5A illustrates hand-crafted diffusion tensor imaging feature maps extracted from eigenvalues of diffusion tensors for mechanisms for brain analysis, in accordance with a representative embodiment.

in FIG. 5A, diffusion tensor imaging (DTI) results on the left and extracted imaging feature maps of several different types on the right, all on a user interface 581, such as on a display 180 in FIG. 1. Feature maps may include images formed by a scalar feature at ever voxel. With feature maps, voxel-wise statistical analyses may be run over a population of spatially aligned healthy and diseased subjects to find statistically significant differences between feature values in certain regions of interest of the brain. Then, explanations can be formed about physical properties of diffusivity which may be indicative of the disease based on the feature being studied.

FIG. 5A shows commonly used hand-crafted diffusion tensor imaging feature maps extracted from the eigenvalues of the diffusion tensors: fractional anisotropy, mean diffusivity, axial diffusivity, radial diffusivity.

Figure 5B:
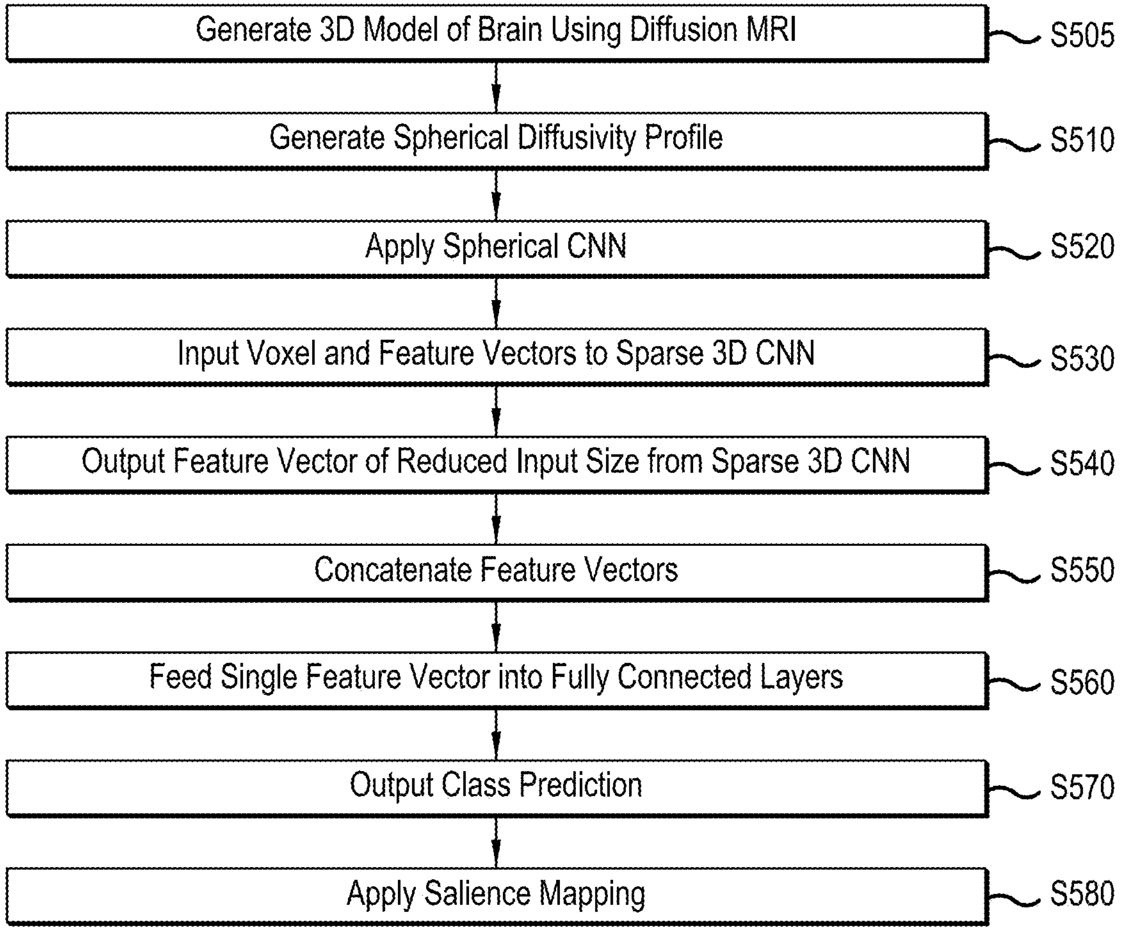
FIG. 5B illustrates a method for mechanisms for brain analysis, in accordance with a representative embodiment.

FIG. 5B illustrates a method for mechanisms for brain analysis, in accordance with a representative embodiment.

The method of FIG. 5B is a method for classifying brain diseases. At S505, a three-dimensional model of a brain is generated using diffusion magnetic resonance imaging.

At S510, a spherical diffusivity profile is generated. The spherical diffusivity profile generated at S510 may be generated for each of a plurality of voxel locations in a three-dimensional model of a brain. The three-dimensional model of the brain may comprise segmented brain regions. Each segmented brain region comprises bundles of neurons connected by fiber tracts.

At S520, a spherical convolutional neural network is applied. The convolutional neural network may be applied to each spherical diffusivity profile to output a feature vector.

At S530, voxel and feature vectors are input from the spherical convolutional neural network to a sparse three-dimensional convolutional neural network. The corresponding voxel and feature vectors may be input for each voxel location for fiber tracts connecting a pair of brain regions in the three-dimensional model of the brain. A sparse three-dimensional convolutional neural network is applied to only the nonzero voxel in the image. The input to the sparse three-dimensional convolutional neural may include the voxel feature values and the voxel coordinates. The voxel values and voxel coordinates may be a data set reduced in size compared to the entire 3D volume size.

At S540, a feature vector of reduced input size is output from the sparse three-dimensional convolutional neural network. The sparse three-dimensional convolutional neural network outputs the feature vector of reduced input size for each voxel location for fiber tracts connecting the pair of brain regions in the three-dimensional model of the brain.

At S550, feature vectors are concatenated. The feature vectors may be concatenated for a plurality of voxel locations for the fiber tracts that connect N region pairs. The feature vectors may be concatenated from the sparse three-dimensional convolutional neural network to form a single feature vector.

At S560, a single feature vector is fed into fully connected layers. That is, the method of FIG. 5B includes feeding the single feature vector into a set of fully connected layers.

At S570, a class prediction is output. The class prediction may be output from the set of fully connected layers, and may classify the health state of the brain as a whole.

At S580, salience mapping is applied. The saliency mapping may be applied to visualize importance of weights of the trained model as heatmaps along fiber tracts connecting regions of interest. The saliency mapping may be applied to visualize importance of individual voxels along the fiber tracts connecting the regions of interest.

Figure 6:
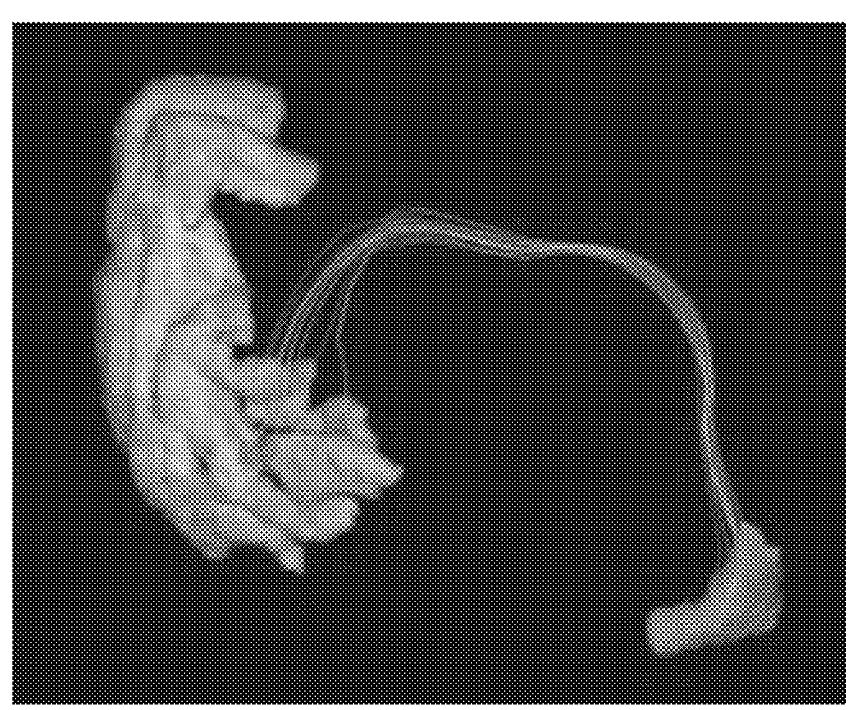
FIG. 6 illustrates structural connectivity of fiber tracts between regions of interests from a brain atlas in mechanisms for brain analysis, in accordance with a representative embodiment.

FIG. 6 illustrates structural connectivity of fiber tracts between regions of interests from a brain atlas in mechanisms for brain analysis, in accordance with a representative embodiment.

In terms of connectivity analysis, features may include hand-crafted connectivity metrics from fiber tractography, such as the number, length, or density of fibers that connect different regions of interest. Additional features may include averaging fractional anisotropy along the voxels occupied by the fiber tracts. This, however, does not incorporate small spatial variations along long fiber tracts over the brain. In FIG. 6, structural connectivity of fiber tracts is illustrated on a user interface 681, such as on a display 180 in FIG. 1.

Figure 7:
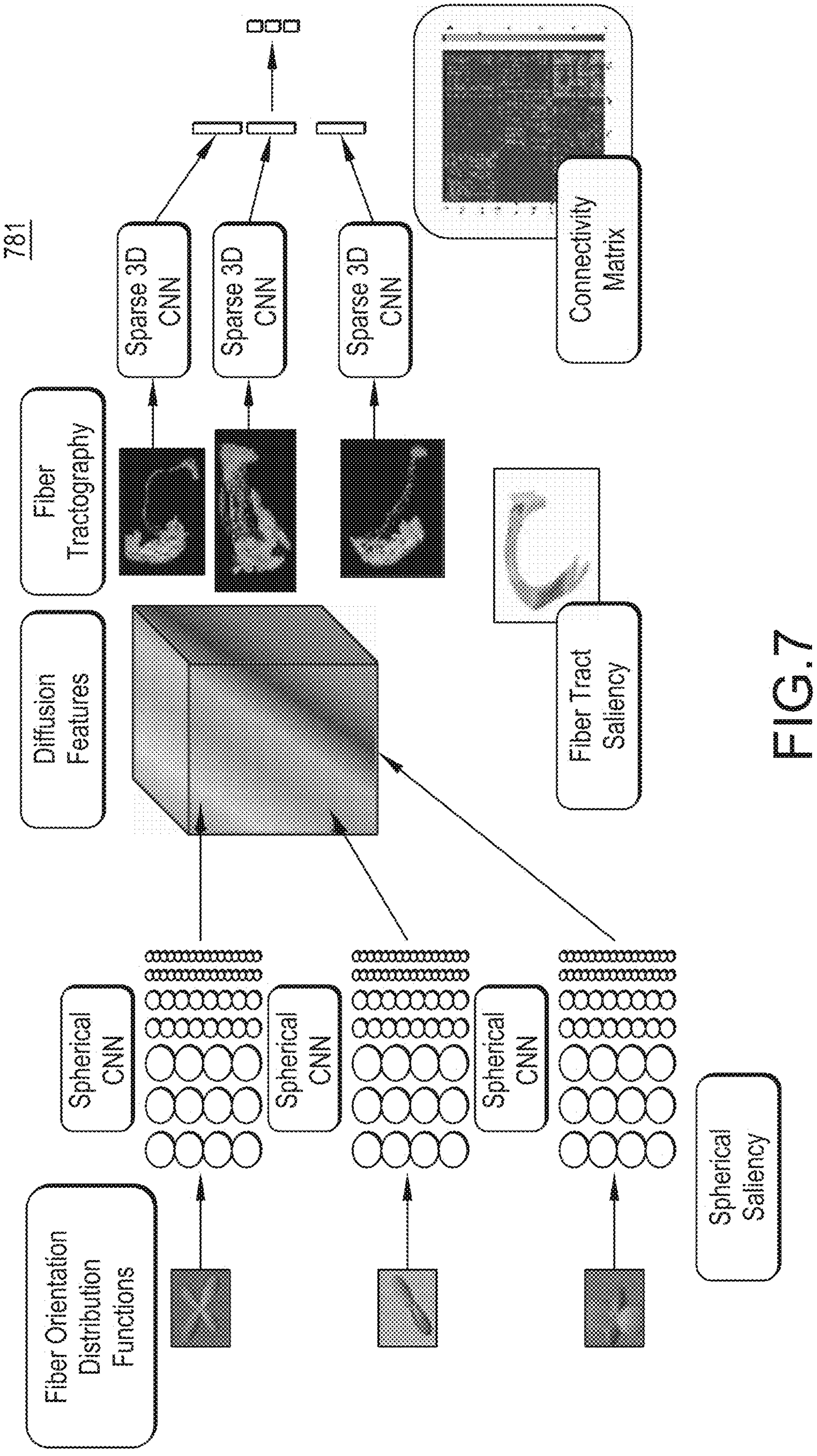
FIG. 7 illustrates an end-to-end deep neural network for structural connectivity based disease classification using spherical convolutional neural networks combined with sparse three-dimensional convolutional neural networks for mechanisms for brain analysis, in accordance with a representative embodiment.

FIG. 7 illustrates an end-to-end deep neural network for structural connectivity based disease classification using spherical convolutional neural networks combined with sparse three-dimensional convolutional neural networks for mechanisms for brain analysis, in accordance with a representative embodiment.

The end-to-end deep neural network in FIG. 7 is shown as on a user interface 781, such as on a display 180 in FIG. 1. The end-to-end deep neural network shown in FIG. 7 may be implemented by the computer 140 in FIG. 1. In FIG. 7, an end-to-end deep learning pipeline is provided for disease classification from orientation distribution functions and tractography reconstructed from diffusion magnetic resonance imaging data. The inputs are 1) spherical (or multi-shell) diffusivity profiles such as fiber orientation distribution functions or orientation distribution functions or multi-shell ensemble average propagators, 2) segmented brain regions of interest from a brain atlas, 3) fiber tracts reconstructed from the diffusivity profile in 1) that connect regions in 2).

From the diffusivity profile such as an fiber orientation distribution functions, a spherical convolutional neural network may be applied to each fiber orientation distribution functions in each voxel. The output of the spherical convolutional neural network is a feature vector of length at least 1. The feature vectors in each voxel are then used as input to the sparse convolutional neural network for each pair of regions of interest that have fiber connections. The input to each sparse convolutional neural network are 1) the voxels occupied by fiber tracts that connect a pair of regions of interest and 2) the set of feature vectors output from the spherical convolutional neural network at each of these voxels. The output of the sparse convolutional neural network is a feature vector of length at least one for each pair of regions of interest. These are then concatenated and fed through fully connected layers and ReLU activations with a final disease class output, e.g., binary or multiclass or regression.

The teachings herein provide an end-to-end deep network starting from the diffusivity profiles and tractography input data and ending at a classification for disease for the whole brain.

In addition, saliency methods can be invoked for deep neural networks which can identify the weights in the network that were responsible for the classification of a new subject. Because the network is divided between inputs for each brain connection, the saliency method can be used to track which brain connections were important for the classification. The relative importance of the brain connections may be visualized with a heatmap along the input voxels and fiber tracts. Furthermore, the saliency to the individual voxels of each important fiber tract and onto the original spherical diffusivity profile can be followed to project a heatmap indicating not only which fiber tract, but also the important voxels along the fiber and the important spherical regions on the diffusivity profile in each voxel.

The pipeline in FIG. 7 is built by connecting neural network components in an end-to-end model. The building starts with voxel locations for fiber tracts that connect N region pairs. Each of the spherical diffusivity profiles is input into a spherical convolutional neural network which is connected as input to a sparse three-dimensional convolutional neural network which outputs a feature vector of reduced input size. These feature vectors are then concatenated to form a single feature vector that is fed into a set of fully connected layers. Finally, a class prediction is output for binary or multi-class classification or regression.

Then a saliency mapping can be applied on a new test subject after classification has been performed in order to visualize the important weights of the network as heatmaps along the voxel regions connecting each region of interest.

Figure 8:
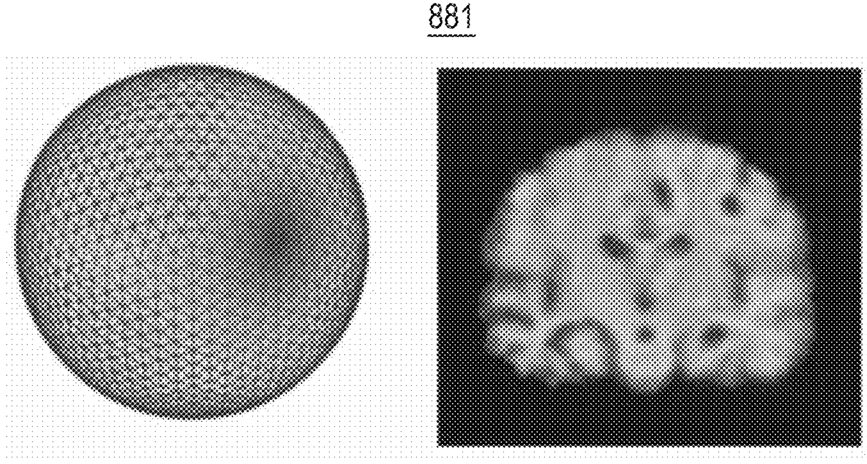
FIG. 8 illustrates a visualization of spherical saliency from a spherical convolutional neural network and a visualization of spatial saliency from a spatial convolutional neural network for mechanisms for brain analysis, in accordance with a representative embodiment.

FIG. 8 illustrates a visualization of spherical saliency from a spherical convolutional neural network and a visualization of spatial saliency from a spatial convolutional neural network for mechanisms for brain analysis, in accordance with a representative embodiment.

In FIG. 8, an example visualization of spherical saliency from a spherical convolutional neural network is shown on the left, and an example visualization of spatial saliency from spatial convolutional neural network is shown on the right. The spherical salience in FIG. 8 is shown as on a user interface 881, such as on a display 180 in FIG. 1.

Figure 9:
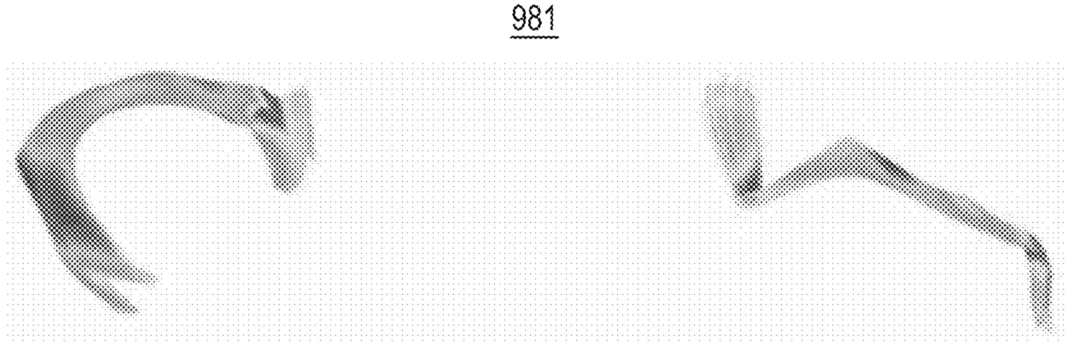
FIG. 9 illustrates visualizations of spatial and spherical saliency maps projected onto fiber tracts for localization of neurological disease in mechanisms for brain analysis, in accordance with a representative embodiment.

FIG. 9 illustrates visualizations of spatial and spherical saliency maps projected onto fiber tracts for localization of neurological disease in mechanisms for brain analysis, in accordance with a representative embodiment.

In FIG. 9, visualizations of spatial and spherical saliency maps are projected onto fiber tracts for localization of neurological disease. The spatial salience map and the spherical saliency map in FIG. 9 are shown as on a user interface 881, such as on a display 180 in FIG. 1.

In a third set of embodiments described herein, structural connectivity maps between brain regions identified in a brain atlas are processed within a deep learning framework for the classification of neurological disease. In the third set of embodiments, graphical convolutional neural networks are applied to brain connectomes derived from structural diffusion magnetic resonance imaging data. Previous graphical convolutional neural networks for the classification of brain connectomes start with hand-crafted structural connectivity features as input to the graph edges, such as the number of fibers that connect each region. This becomes a limited representation of the complex diffusion magnetic resonance imaging data used to construct the graph. In the third set of embodiments, fixed hand-crafted structural connectivity features are replaced with data-driven features from a neural network that extracts richer information from the diffusion magnetic resonance imaging data. Specifically, a combination of sparse three-dimensional convolutional neural networks produce features for each edge of the graph in a single end-to-end neural network. In addition, because each fiber connection is taken as multiple inputs to the network, using a gradient based saliency mapping, the contribution of each fiber connection to the end classification may be visualized.

As noted above, in terms of connectivity analysis, features may include hand-crafted connectivity metrics from fiber tractography, such as the number, length, or density of fibers that connect different regions of interest. Additional features may include averaging fractional anisotropy along the voxels occupied by the fiber tracts. These features may be used as an indication of the strength of fiber connections from one region of the brain to another, or edges in a graph, where nodes are the regions of interest defined by a segmented T1w brain atlas.

Given a brain graph, a standard method to understand changes in brain connectivity with respect to a neurological disease is to statistically monitor changes in graph metrics between populations, as related to node degree, hubs, efficiency, and local and global network properties. Instead of applying graphical convolutional neural networks on hand-crafted edge features, such as the number of fiber tracts which are highly dependent on the processing and tractography algorithms and do not give a full picture of the diffusion magnetic resonance imaging data acquired, the third set of embodiments incorporates an additional neural network to extract rich features from diffusion magnetic resonance imaging data as input to the graphical convolutional neural network in a single end-to-end deep neural network for brain classification.

The third set of embodiments provide a graphical convolutional neural network for diffusion magnetic resonance imaging classification with deep structural connectivity features using sparse three-dimensional convolutional neural networks.

Figure 10A:
FIG. 10A illustrates an end-to-end deep neural network using sparse three-dimensional convolutional neural networks combined with graphical convolutional neural networks for mechanisms for brain analysis, in accordance with a representative embodiment.
Figure 11:
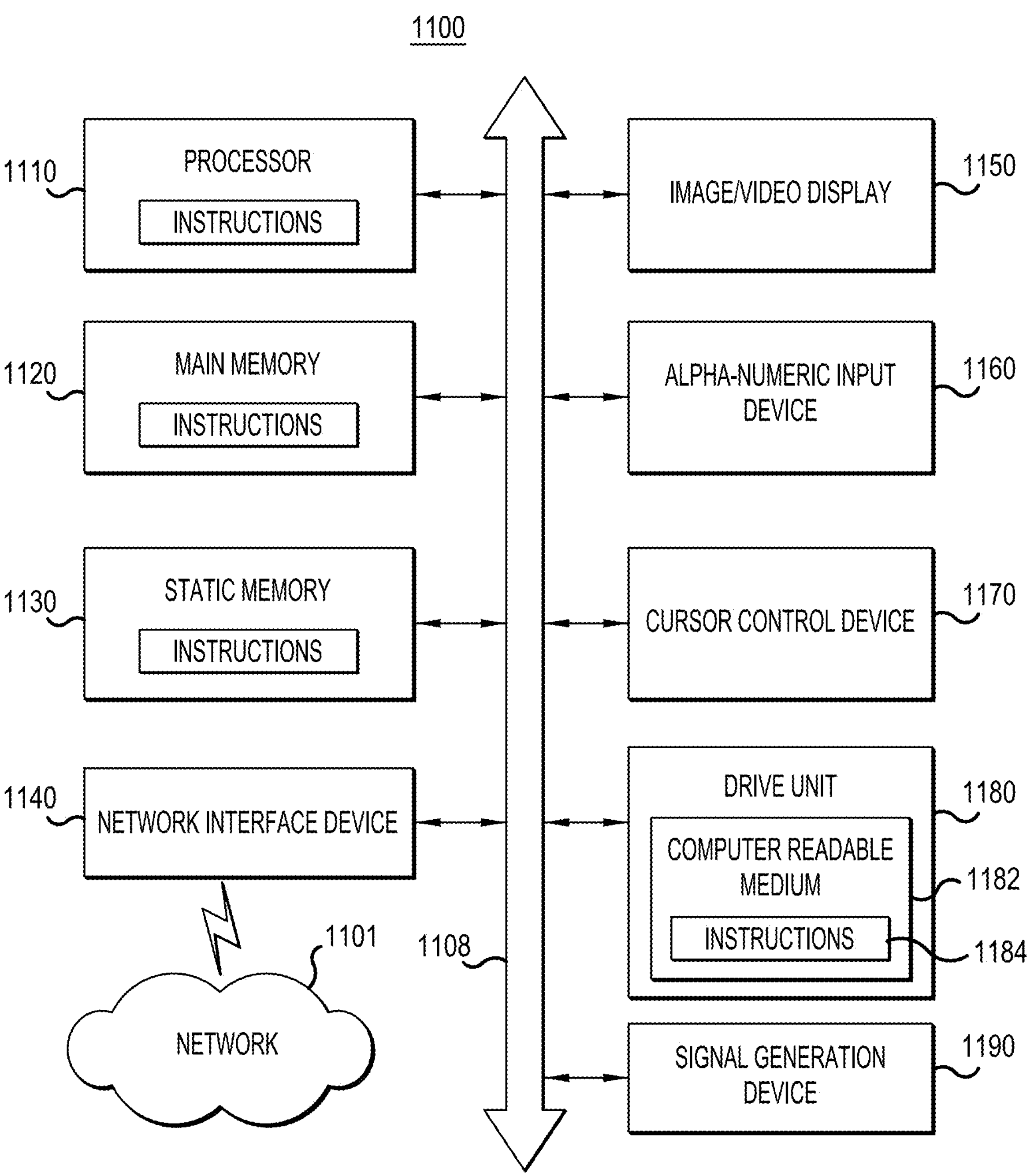
FIG. 11 illustrates a computer system, on which a method for mechanisms for brain analysis is implemented, in accordance with another representative embodiment.

FIG. 10A illustrates an end-to-end deep neural network using sparse three-dimensional convolutional neural networks combined with graphical convolutional neural networks for mechanisms for brain analysis, in accordance with a representative embodiment.

Figure 10A:
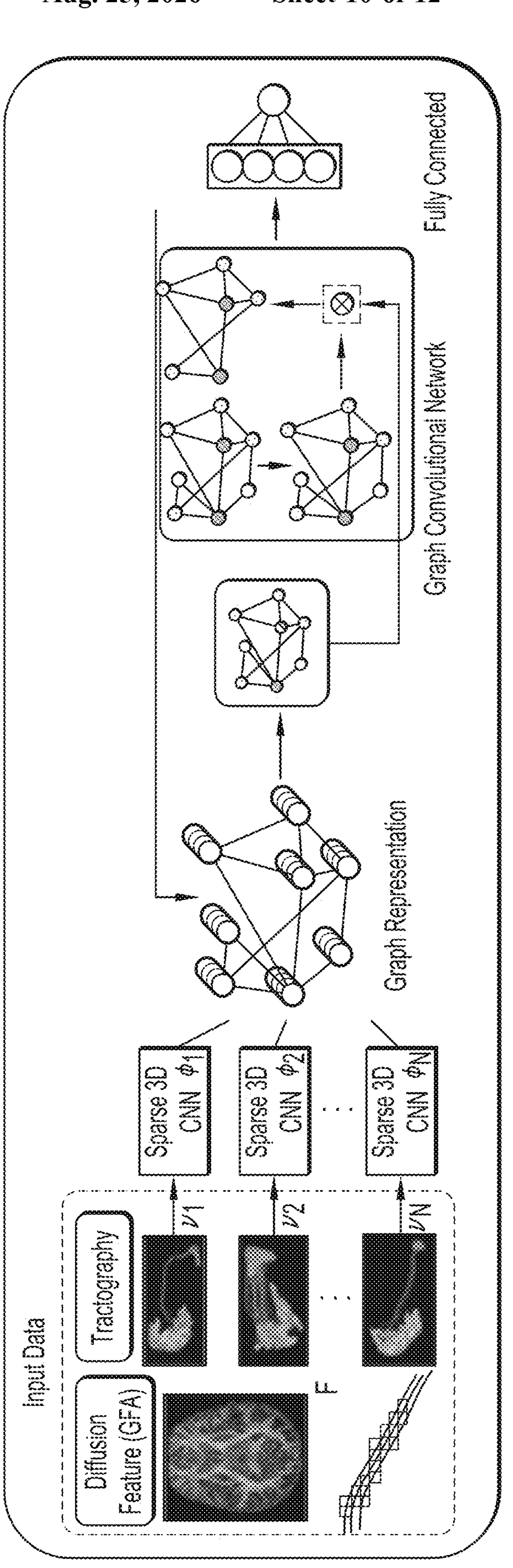

The end-to-end deep neural network in FIG. 10 is shown as on a user interface 1081, such as on a display 180 in FIG. 1. The end-to-end deep neural network shown in FIG. 10A may be implemented by the computer 140 in FIG. 1. In FIG. 10A, an end-to-end deep network starts from the diffusivity profiles and tractography input data and ends at a classification for disease for the whole brain. The inputs are 1) segmented brain regions of interest from a T1 W brain atlas, 2) fiber tracts reconstructed from the diffusion magnetic resonance imaging using tractography and 3) features from the orientation distribution functions such as fractional anisotropy.

The end-to-end deep neural network in FIG. 10A consists of two main elements: 1) set of Sparse three-dimensional convolutional neural networks, one for each pair of regions of interest, fed into a single 2) a graphical convolutional neural network. The inputs to each sparse three-dimensional convolutional neural network are 1) the voxels occupied by fiber tracts that connect a pair of regions of interest and 2) the set of features of the orientation distribution functions at each voxel, e.g., fractional anisotropy. The output of the sparse convolutional neural network convolutional neural network is a feature vector of length at least one for each pair of regions of interest and are edge feature inputs to the graphical convolutional neural network. The output of the graphical convolutional neural network will be a set of feature layers that are fed through a fully connected layer, nonlinear activation and a final disease class output, e.g., binary, multiclass, or regression. In addition, saliency methods for deep neural networks may be invoked. The saliency methods can identify the weights in the network that were responsible for the classification of a new subject. Because the network is divided between inputs for each brain connection, the saliency method is used to track which brain connections were important for the classification. The brain connections may be visualized with a heatmap along the input voxels and fiber tracts.

The end-to-end deep neural network in FIG. 10A may be built by connecting neural network components in an end-to-end model. The building may start with voxel locations for fiber tracts that connect N region pairs. Each fiber tract connection and the features occupied by the voxels of the fiber tracts are input to a sparse three-dimensional convolutional neural network which outputs a feature vector of reduced input size. These feature vectors are then input as edge features to the graphical convolutional neural network which output to a set of fully connected layers and nonlinear activations and finally outputs a class prediction for binary or multi-class classification or regression.

Additionally, a saliency mapping can then be applied on a new test subject after classification has been performed in order to visualize the important weights of the network as heatmaps along the voxel regions connecting each region of interest.

Figure 10B:
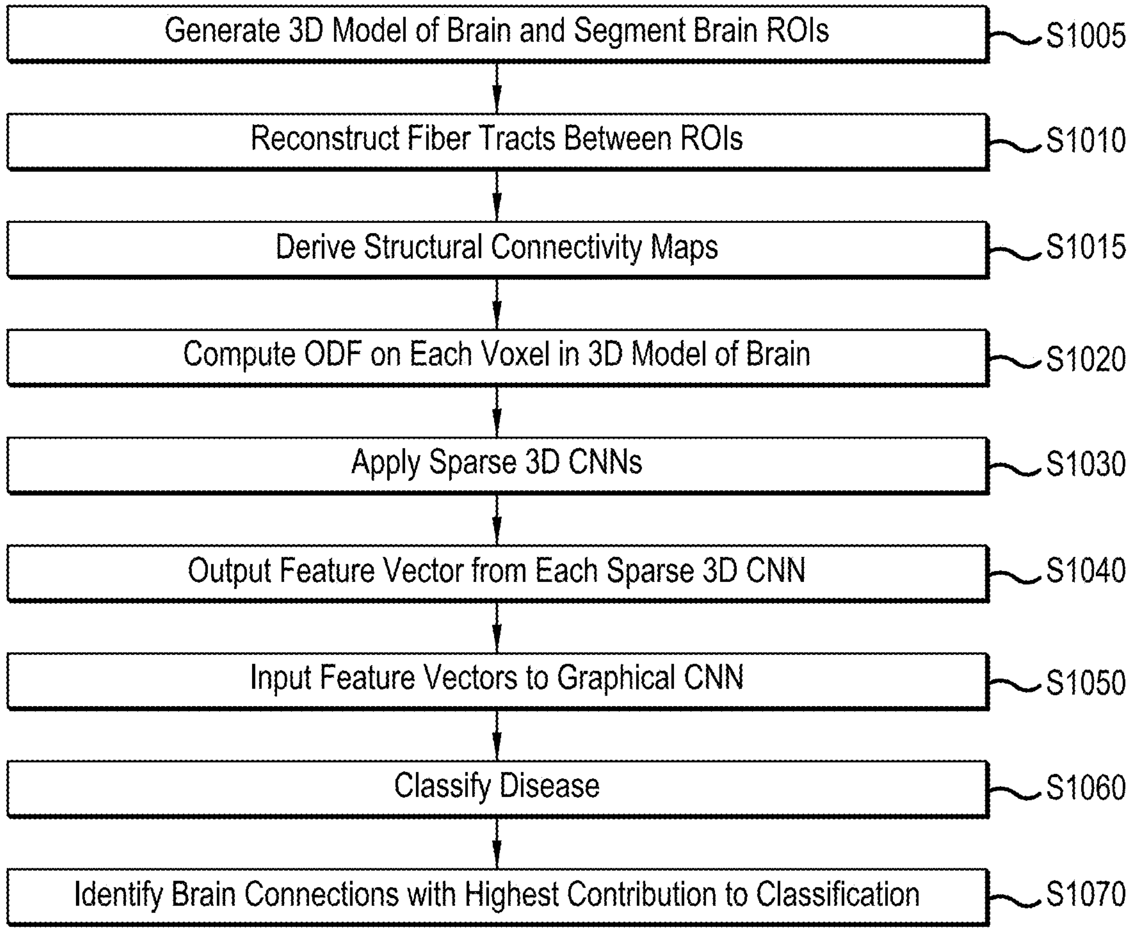
FIG. 10B illustrates a method for mechanisms for brain analysis, in accordance with a representative embodiment.

FIG. 10B illustrates a method for mechanisms for brain analysis, in accordance with a representative embodiment.

At S1005, a three-dimensional model of a brain is generated, and brain regions of interest are segmented. The three-dimensional model of the brain is a digital model. The brain regions of interest are segmented from the three-dimensional digital model of the brain.

At S1010, fiber tracts between the regions of interest are reconstructed. The fiber tracts are reconstructed from structural diffusion magnetic resonance imaging data by following peaks of spherical probability distribution functions in each of a plurality of voxels in the digital model of the brain.

At S1015, structural connectivity maps are derived.

At S1020, an orientation distribution function is computed on each voxel in the three-dimensional model of the brain.

At S1030, sparse three-dimensional convolutional neural networks are applied. The sparse convolutional neural networks are applied to the segmented brain regions of interest, to the reconstructed fiber tracts, and to features form the orientation distribution function of the brain. As an example, a different sparse three-dimensional convolutional neural network is provided for each pair of regions of interest. Each of the sparse convolutional neural networks may be applied to voxels occupied by the reconstructed fiber tracts and a set of features of the orientation distribution function at east of the voxels.

At S1040, a feature vector is output from each sparse three-dimensional convolutional neural network.

At S1050 feature vectors are input to a graphical convolutional neural network. In some embodiments, each spare three-dimensional convolutional neural network outputs to the graphical convolutional neural network a feature vector with a length of at least one for each pair of regions of interest. The graphical convolutional neural network outputs a set of feature layers that are fed through a fully connected layer, a nonlinear activation and a final disease classification output.

At S1060 disease is classified. The classification may be binary or along a scale with more than two possible outcomes.

At S1070, brain connections with the highest contribution to the classification are identified.

In another embodiment, spherical convolutional neural networks may be used to extract deep features from the orientation distribution functions which can be fed into the sparse convolutional neural network. This embodiment would include three main elements instead of the two shown in FIG. 10A. The three elements include a spherical convolutional neural network for each voxel, a sparse three-dimensional convolutional neural network for each pair of regions of interest and a graphical convolutional neural network combined end-to-end to predict neurological disease.

FIG. 11 illustrates a computer system, on which a method for mechanisms for brain analysis is implemented, in accordance with another representative embodiment.

Referring to FIG. 11, the computer system 1100 includes a set of software instructions that can be executed to cause the computer system 1100 to perform any of the methods or computer-based functions disclosed herein. The computer system 1100 may operate as a standalone device or may be connected, for example, using a network 1101, to other computer systems or peripheral devices. In embodiments, a computer system 1100 performs logical processing based on digital signals received via an analog-to-digital converter.

In a networked deployment, the computer system 1100 operates in the capacity of a server or as a client user computer in a server-client user network environment, or as a peer computer system in a peer-to-peer (or distributed) network environment. The computer system 1100 can also be implemented as or incorporated into various devices, such as a workstation that includes a controller, a stationary computer, a mobile computer, a personal computer (PC), a laptop computer, a tablet computer, or any other machine capable of executing a set of software instructions (sequential or otherwise) that specify actions to be taken by that machine. The computer system 1100 can be incorporated as or in a device that in turn is in an integrated system that includes additional devices. In an embodiment, the computer system 1100 can be implemented using electronic devices that provide voice, video or data communication. Further, while the computer system 1100 is illustrated in the singular, the term "system" shall also be taken to include any collection of systems or sub-systems that individually or jointly execute a set, or multiple sets, of software instructions to perform one or more computer functions.

As illustrated in FIG. 11, the computer system 1100 includes a processor 1110. The processor 1110 may be considered a representative example of a processor of a controller and executes instructions to implement some or all aspects of methods and processes described herein. The processor 1110 is tangible and non-transitory. As used herein, the term "non-transitory" is to be interpreted not as an eternal characteristic of a state, but as a characteristic of a state that will last for a period. The term "non-transitory" specifically disavows fleeting characteristics such as characteristics of a carrier wave or signal or other forms that exist only transitorily in any place at any time. The processor 1110 is an article of manufacture and/or a machine component. The processor 1110 is configured to execute software instructions to perform functions as described in the various embodiments herein. The processor 1110 may be a general-purpose processor or may be part of an application specific integrated circuit (ASIC). The processor 1110 may also be a microprocessor, a microcomputer, a processor chip, a controller, a microcontroller, a digital signal processor (DSP), a state machine, or a programmable logic device. The processor 1110 may also be a logical circuit, including a programmable gate array (PGA), such as a field programmable gate array (FPGA), or another type of circuit that includes discrete gate and/or transistor logic. The processor 1110 may be a central processing unit (CPU), a graphics processing unit (GPU), or both. Additionally, any processor described herein may include multiple processors, parallel processors, or both. Multiple processors may be included in, or coupled to, a single device or multiple devices.

The term "processor" as used herein encompasses an electronic component able to execute a program or machine executable instruction. References to a computing device comprising "a processor" should be interpreted to include more than one processor or processing core, as in a multi-core processor. A processor may also refer to a collection of processors within a single computer system or distributed among multiple computer systems. The term computing device should also be interpreted to include a collection or network of computing devices each including a processor or processors. Programs have software instructions performed by one or multiple processors that may be within the same computing device or which may be distributed across multiple computing devices.

The computer system 1100 further includes a main memory 1120 and a static memory 1130, where memories in the computer system 1100 communicate with each other and the processor 1110 via a bus 1108. Either or both of the main memory 1120 and the static memory 1130 may be considered representative examples of a memory of a controller, and store instructions used to implement some or all aspects of methods and processes described herein. Memories described herein are tangible storage mediums for storing data and executable software instructions and are non-transitory during the time software instructions are stored therein. As used herein, the term "non-transitory" is to be interpreted not as an eternal characteristic of a state, but as a characteristic of a state that will last for a period. The term "non-transitory" specifically disavows fleeting characteristics such as characteristics of a carrier wave or signal or other forms that exist only transitorily in any place at any time. The main memory 1120 and the static memory 1130 are articles of manufacture and/or machine components. The main memory 1120 and the static memory 1130 are computer-readable mediums from which data and executable software instructions can be read by a computer (e.g., the processor 1110). Each of the main memory 1120 and the static memory 1130 may be implemented as one or more of random access memory (RAM), read only memory (ROM), flash memory, electrically programmable read only memory (EPROM), electrically erasable programmable read-only memory (EEPROM), registers, a hard disk, a removable disk, tape, compact disk read only memory (CD-ROM), digital versatile disk (DVD), floppy disk, blu-ray disk, or any other form of storage medium known in the art. The memories may be volatile or non-volatile, secure and/or encrypted, unsecure and/or unencrypted.

"Memory" is an example of a computer-readable storage medium. Computer memory is any memory which is directly accessible to a processor. Examples of computer memory include, but are not limited to RAM memory, registers, and register files. References to "computer memory" or "memory" should be interpreted as possibly being multiple memories. The memory may for instance be multiple memories within the same computer system. The memory may also be multiple memories distributed amongst multiple computer systems or computing devices.

As shown, the computer system 1100 further includes a video display unit 1150, such as a liquid crystal display (LCD), an organic light emitting diode (OLED), a flat panel display, a solid-state display, or a cathode ray tube (CRT), for example. Additionally, the computer system 1100 includes an input device 1160, such as a keyboard/virtual keyboard or touch-sensitive input screen or speech input with speech recognition, and a cursor control device 1170, such as a mouse or touch-sensitive input screen or pad. The computer system 1100 also optionally includes a disk drive unit 1180, a signal generation device 1190, such as a speaker or remote control, and/or a network interface device 1140.

In an embodiment, as depicted in FIG. 11, the disk drive unit 1180 includes a computer-readable medium 1182 in which one or more sets of software instructions 1184 (software) are embedded. The sets of software instructions 1184 are read from the computer-readable medium 1182 to be executed by the processor 1110. Further, the software instructions 1184, when executed by the processor 1110, perform one or more steps of the methods and processes as described herein. In an embodiment, the software instructions 1184 reside all or in part within the main memory 1120, the static memory 1130 and/or the processor 1110 during execution by the computer system 1100. Further, the computer-readable medium 1182 may include software instructions 1184 or receive and execute software instructions 1184 responsive to a propagated signal, so that a device connected to a network 1101 communicates voice, video or data over the network 1101. The software instructions 1184 may be transmitted or received over the network 1101 via the network interface device 1140.

In an embodiment, dedicated hardware implementations, such as application-specific integrated circuits (ASICs), field programmable gate arrays (FPGAs), programmable logic arrays and other hardware components, are constructed to implement one or more of the methods described herein. One or more embodiments described herein may implement functions using two or more specific interconnected hardware modules or devices with related control and data signals that can be communicated between and through the modules. Accordingly, the present disclosure encompasses software, firmware, and hardware implementations. Nothing in the present application should be interpreted as being implemented or implementable solely with software and not hardware such as a tangible non-transitory processor and/or memory.

In accordance with various embodiments of the present disclosure, the methods described herein may be implemented using a hardware computer system that executes software programs. Further, in an exemplary, non-limited embodiment, implementations can include distributed processing, component/object distributed processing, and parallel processing. Virtual computer system processing may implement one or more of the methods or functionalities as described herein, and a processor described herein may be used to support a virtual processing environment.

Accordingly, mechanisms for brain analysis enables multiple uses for analysis of brain images by end-to-end deep neural networks. For example, end-to-end deep neural networks may be applied to brain images to predict whether individual fiber connections which connect connected brain regions are indicative of a healthy brain or a diseased brain. End-to-end deep neural networks may be applied to brain images to output a class prediction for the brain as a whole. End-to-end deep neural networks may be applied to brain images to classify a disease for the brain.

Although mechanisms for brain analysis has been described with reference to several exemplary embodiments, it is understood that the words that have been used are words of description and illustration, rather than words of limitation. Changes may be made within the purview of the appended claims, as presently stated and as amended, without departing from the scope and spirit of mechanisms for brain analysis in its aspects. Although mechanisms for brain analysis has been described with reference to particular means, materials and embodiments, mechanisms for brain analysis is not intended to be limited to the particulars disclosed; rather mechanisms for brain analysis extends to all functionally equivalent structures, methods, and uses such as are within the scope of the appended claims.

The illustrations of the embodiments described herein are intended to provide a general understanding of the structure of the various embodiments. The illustrations are not intended to serve as a complete description of all of the elements and features of the disclosure described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is provided to comply with 37 C.F.R. § 1.72(b) and is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

The preceding description of the disclosed embodiments is provided to enable any person skilled in the art to practice the concepts described in the present disclosure. As such, the above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents and shall not be restricted or limited by the foregoing detailed description.

The invention claimed is:

1. A method for localizing structural connectivity biomarkers in neurological diseases, comprising:

dividing a diffusion magnetic resonance imaging brain volume into a set of connected brain regions;

extracting three-dimensional voxels along fiber connections which structurally connect the connected brain regions, wherein the connected brain regions comprise bundles of neurons;

applying a deep neural network to diffusion magnetic resonance imaging features extracted from the three-dimensional voxels for each set of fiber connections which structurally connect brain regions;

defining, for multi-instance learning, each instance as a fiber connection that structurally connects a pair of segmented brain regions delineated by a brain atlas;

producing, via a Sigmoid layer of the deep neural network, a probabilistic class score for each fiber connection indicating a positive or negative label for the presence or absence of a specified neurological disease;

aggregating the per-fiber-connection probabilistic class scores in a final multi-instance learning layer to produce a brain-level classification, wherein the brain-level classification is based on the aggregation, and outputting the brain-level classification; and outputting a set of fiber-connection locations and the corresponding probabilistic class scores to provide a connection-wise probabilistic localization of a disease biomarker.

2. The method of claim 1, wherein the multi-instance learning is further applied to identify relative importance of fiber connections in contributing to a disease.

3. The method of claim 1, further comprising:

determining weightings of fiber connections to identify a relative importance of fiber connections in contributing to a disease; and generating a heat map to visualize the relative importance of fiber connections based on the weightings.

4. The method of claim 1, further comprising:

reconstructing the fiber connections using diffusion magnetic resonance imaging.

5. The method of claim 1, further comprising:

localizing a disease to a particular set of fiber connections and relating the fiber connections of the particular set to fiber tractography using global brain-volume labels.

6. The method of claim 1, wherein applying multi-instance learning comprises:

processing a diffusion magnetic resonance imaging volume using fiber tractography into a set of fiber connections that connect a set of brain regions delineated by a brain atlas, wherein the multi-instance learning is applied by a deep neural network, the Sigmoid layer which produces the probabilistic class score for each fiber connection, and a final multi-instance learning layer that aggregates the probabilistic class scores to produce the brain-level classification and relates fiber-connection scores to an image of the brain.

7. The method of claim 6, further comprising:

determining a maximum score over all fiber connections.

8. The method of claim 7, further comprising:

outputting a brain class prediction based on the maximum of the probabilistic class scores over the fiber connections; and outputting a set of fiber-connection locations and probabilistic class scores providing a connection-wise probabilistic localization of a disease biomarker.

9. A system for localizing structural connectivity biomarkers in neurological diseases, comprising:

a memory that stores instructions;

a display; and a processor that executes the instructions, wherein based on the processor executing the instructions, the system is caused to:

divide a diffusion magnetic resonance imaging brain volume into a set of connected brain regions;

extract three-dimensional voxels along fiber connections which structurally connect the connected brain regions, wherein the connected brain regions comprise bundles of neurons;

apply a deep neural network to diffusion magnetic resonance imaging features extracted from the three-dimensional voxels for each set of fiber connections which structurally connect brain regions;

apply multi-instance learning in which each instance corresponds to a fiber connection that structurally connects a pair of segmented brain regions delineated by a brain atlas, including producing, via a Sigmoid layer of the deep neural network, a probabilistic class score for each fiber connection indicating a positive or negative label for the presence or absence of a specified neurological disease, aggregating the per-fiber-connection probabilistic class scores in a final multi-instance learning layer to produce a brain-level classification, and output the brain-level classification; and output a set of fiber-connection locations and the corresponding probabilistic class scores to provide a connection-wise probabilistic localization of a disease biomarker.

10. The system of claim 9, wherein the multi-instance learning is further applied to identify relative importance of fiber connections in contributing to a disease.

11. The system of claim 9, wherein based on the processor executing the instructions, the system is further caused to:

determine weightings of fiber connections to identify the relative importance of fiber connections in contributing to a disease; and generate a heat map to visualize the relative importance of fiber connections based on the weightings.

12. The system of claim 9, wherein based on the processor executing the instructions, the system is further caused to:

reconstruct the fiber connections using diffusion magnetic resonance imaging.

13. The system of claim 9, wherein based on the processor executing the instructions, the system is further caused to:

localize a disease to a particular set of fiber connections and relate the fiber connections of the particular set to fiber tractography using global brain-volume labels.

14. The system of claim 9, wherein based on the processor executing the instructions, the system is further caused to apply the multi-instance learning by:

processing a diffusion magnetic resonance imaging volume using fiber tractography into a set of fiber connections that connect a set of brain regions delineated by a brain atlas, wherein the multi-instance learning is applied by a deep neural network, a Sigmoid layer which produces a probabilistic class score for each fiber connection, and a final multi-instance learning layer that aggregates the probabilistic class scores to produce the brain-level classification and relates fiber-connection scores to an image of the brain.

15. The system of claim 9, wherein based on the processor executing the instructions, the system is further caused to:

determine a maximum score over all fiber connections.

16. The system of claim 15, wherein based on the processor executing the instructions, the system is further caused to:

output a brain class prediction based on the maximum of the probabilistic class scores over the fiber connections; and output a set of fiber-connection locations and probabilistic class scores providing a connection-wise probabilistic localization of a disease biomarker.

17. A controller for localizing structural connectivity biomarkers in neurological diseases, comprising:

a memory that stores instruction; and a processor that executes the instructions, wherein based on the processor executing the instructions, the controller is caused to:

divide a diffusion magnetic resonance imaging brain volume into a set of connected brain regions;

extract three-dimensional voxels along fiber connections which structurally connect the connected brain regions, wherein the connected brain regions comprise bundles of neurons;

apply a deep neural network to diffusion magnetic resonance imaging features extracted from the three-dimensional voxels for each set of fiber connections which structurally connect brain regions;

apply multi-instance learning in which each instance corresponds to a fiber connection that structurally connects a pair of segmented brain regions delineated by a brain atlas, including producing, via a Sigmoid layer of the deep neural network, a probabilistic class score for each fiber connection indicating a positive or negative label for the presence or absence of a specified neurological disease, aggregating the per-fiber-connection probabilistic class scores in a final multi-instance learning layer to produce a brain-level classification, and output the brain-level classification; and output a set of fiber-connection locations and the corresponding probabilistic class scores to provide a connection-wise probabilistic localization of a disease biomarker.

* * * * *